United States Patent [19]

Bailey et al.

[11] Plant 4,572

[45] Jul. 15, 1980

[54] PEACH CULTIVAR

[75] Inventors: Catherine H. Bailey, Englishtown; L. Fredric Hough, Bloomsbury, both of N.J.

[73] Assignee: Stark Brothers Nurseries & Orchards Company, Louisiana, Mo.

[21] Appl. No.: 24,713

[22] Filed: Mar. 28, 1979

[51] Int. Cl.[2] ..... A01H 5/03

[52] U.S. Cl. ..... Plt./43

[58] Field of Search ..... Plt./43

*Primary Examiner*—Robert E. Bagwill

*Attorney, Agent, or Firm*—Burns, Doane, Swecker & Mathis

[57] ABSTRACT

A new and distinct peach variety which originated by the crossing of an unnamed New Jersey seedling No. 585414 with pollen from the Autumnglo variety is provided. This new variety is a late maturing yellow freestone peach variety which bears large round firm fruit having an attractive bright red skin color (as illustrated). The fruit flesh is golden yellow in color, and slow softening with a superior rich and delicious flavor. The fruit buds exhibit exceptionally good winter hardiness. Also, the variety has exhibited improved tolerance to common bacterial leaf spot disease.

5 Drawing Figures

SUMMARY OF THE INVENTION

The new and distinct variety of peach tree originated through the hand pollination of unnamed New Jersey seedling No. 585414 with pollen from the Autumnglo variety (non-patented). The resulting seed from these hand pollinated flowers was germinated in a greenhouse during the winter of 1968–1969 and was planted out-of-doors during the spring of 1969 at the New Jersey Agriculture Experiment Station in Cream Ridge, N.J. Tree 88 of Row 27 of this planting first fruited in 1971 and originally was selected because of the large size of the fruit, its attractiveness, and season of maturity. This seedling was then designated C1R27T88. In 1972 after a very severe late winter freeze seedling C1R27T88 had only approximately 25 to 50 percent of its fruit buds killed while most other peach varieties growing in the area had 100 percent loss of fruit buds.

During the summer of 1973 a few trees of C1R27T88 were asexually reproduced by budding so that they could be further evaluated. After continued evaluation for large fruit size, attractiveness, consistency of production, and hardiness to low winter temperatures, this new variety was selected for advance testing and was designated NJ 260. Such testing confirmed the merit of the variety and during the fall of 1977 it was submitted to the New Jersey Peach Council for further testing and evaluation.

Trees of the new variety have exhibited a strong vigorous growth habit, exceptional winter hardiness of the fruit buds, improved tolerance to common bacterial leaf spot (i.e., *Xanthomonas pruni*), and the ability productively to form globose large round firm fruit having an attractive bright red skin color (as illustrated). The fruit flesh is golden yellow in color and slow softening with a superior rich and delicious flavor. The fruit commonly ripens very late with that of the Autumnglo variety (unpatented) and approximately 3 to 5 days after that of the Rio Oso Gem variety (U.S. Plant Patent No. 84). Other peach varieties growing in the same area bearing fruit in the same season of maturity as the present variety have tended to be badly infected with the bacterial leaf spot.

Asexual propagation of the new variety beginning in 1973 has demonstrated that its combination of characteristics comes true to form and is established and transmitted through succeeding generations. The specimens described herein were grown and observed at Cream Ridge, N.J.

BRIEF DESCRIPTION OF THE PHOTOGRAPH

The accompanying photograph shows typical specimens of the fruit and foliage of our new variety as depicted in color as nearly true as it is reasonably possible to make the same in a color illustration of this character.

DETAILED DESCRIPTION OF NEW VARIETY

Dates of first and last pickings: September 12 and September 21.

Tree: Large size; vigorous; spreading; hardy; productive; regular bearer.

- *Trunk.*—Medium stocky.
- *Branches.*—Medium stocky. Lenticels— medium small.
- *Leaves.*—Abruptly pointed; medium thick; smooth. Length— approximately $6\frac{1}{4}$ to $7\frac{1}{4}$ inches. Width— approximately $1\frac{1}{4}$ to $1\frac{3}{8}$ inches. Color— medium green — Forest Green Plate XVII 29 m, Ridgeway's Color Standards. Margin— crenate. Petiole— medium long; medium thick. Glands— average number: 3; opposite; medium large; reniform.

Flowers:

- *Date of first blossoms.*—April 12; late.
- *Size.*—Medium to small; non-showy.
- *Color.*—Pink — Deep Rose Pink Plate X 11 71-d, Ridgeway's Color Standards.

Fruit:

- *Maturity when described.*—Hard; under ripe; date—September 15.
- *Size.*—Large. Axial diameter— Approximately $2\frac{1}{2}$ to $3\frac{3}{4}$ inches. Transverse in suture planes— approximately $2\frac{5}{8}$ to 3 inches. At right angles to suture planes—approximately $2\frac{5}{8}$ to 3 inches.
- *Form.*—Uniform; symmetrical; globose; ovoid.
- *Suture.*—Shallow; extends from base to apex.
- *Ventral surface.*—Rounded; slightly ridged on either side.

*Cavity.*—Rounded; abrupt; generally circular; very slightly elongated. Depth— ½ inch. Breadth— ½ inch. Markings— yellowish green undercolor with mostly all orange red to red.

*Base.*—Retuse.

*Apex.*—Emarginate.

*Stem.*—Short length; pubescent; medium.

*Skin.*—Medium thick; free; slight in wet season. Color— highly blushed red; approximately 75 to 85 percent of blush mostly Brazil Red 1-5-i to Peach Red 1-5-b, Ridgeway's Color Standards, and approximately 15 to 25 percent green yellow undercolor on side not exposed to sun; does roll up when rubbed.

Flesh:

*Color.*—Yellow; mottled with red next to skin.

*Surface of pit cavity.*—Yellow with pink fibers.

*Amygdalin.*—Scant; abundant.

*Texture.*—Firm.

*Fibers.*—Fine.

*Ripens.*—Fairly even.

*Flavor.*—Subacid; mild.

*Aroma.*—Distinct.

*Eating quality.*—Good.

Stone: Free.

*Fibers.*—Parts from flesh smoothly.

*Size.*—Medium large.

Length— approximately 1¼ to 1½ inches. Thickness— approximately ⅞ to 1¼ inches.

*Form.*—Apex acuminate.

*Base.*—Oval.

*Apex.*—Acuminate.

*Sides.*—Mostly equal.

*Surface.*—Furrowed near base; pitted throughout.

Use: Market; dessert.

Keeping quality: Good.

Resistance to insects: Good.

Resistance to diseases: Good.

Shipping quality: Good.

We claim:

1. A new and distinct variety of yellow freestone peach tree, substantially as illustrated and described, characterized by a strong, vigorous growth habit, the exceptional winter hardiness of the fruit buds, improved tolerance to bacterial leaf spot, and the ability to yield large round firm globose bright red colored slow softening fruit having a rich and delicious flower which commonly ripens very late with that of the Autumnglo variety and approximately 3 to 5 days after that of the Rio Oso Gem variety.

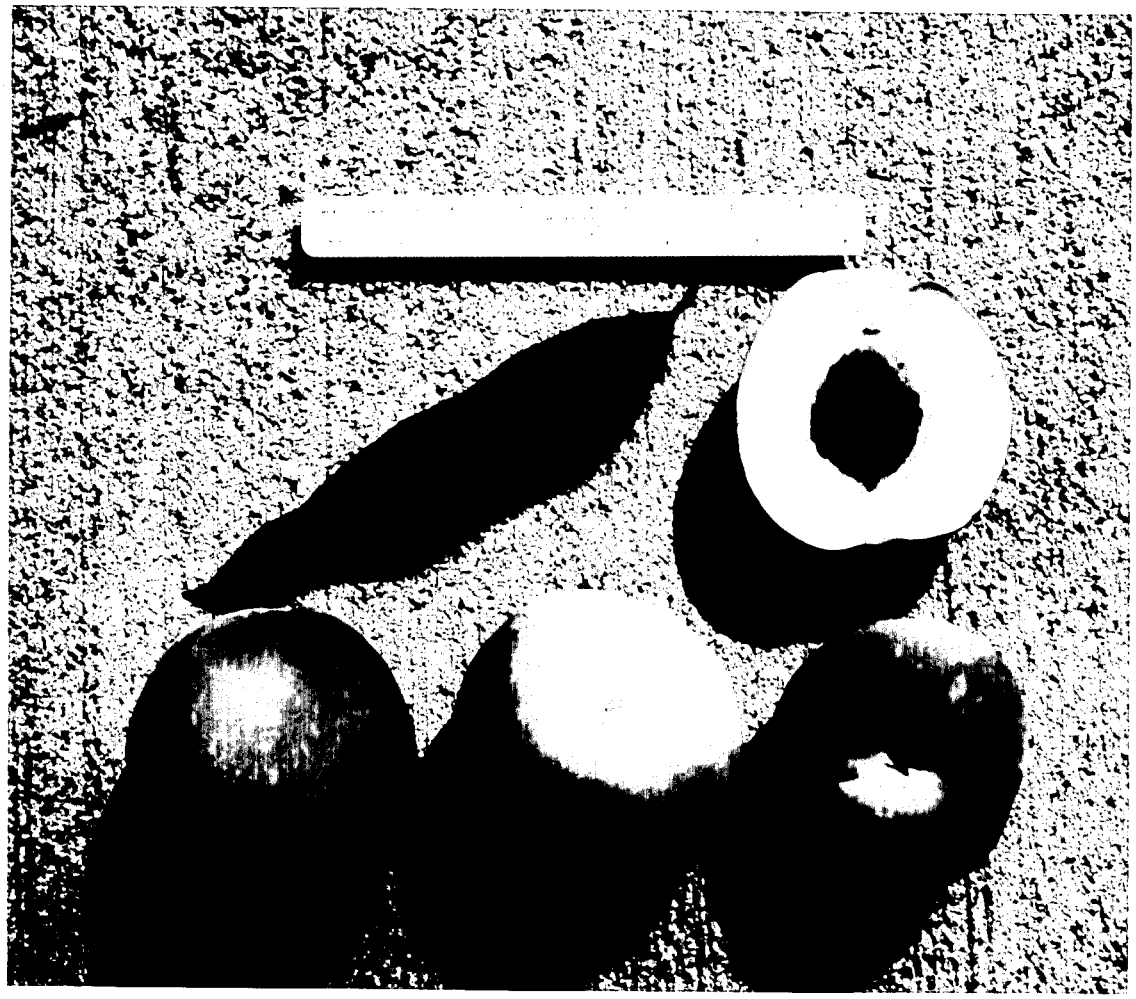

* * * * *